US00PP08744P

United States Patent [19]

Thiara

[11] Patent Number: Plant 8,744

[45] Date of Patent: May 24, 1994

[54] PEACH TREE, "THIARA"

[76] Inventor: Sarbjit Thiara, 1896 Jacob Dr., Yuba City, Calif. 95991

[21] Appl. No.: 994,621

[22] Filed: Dec. 21, 1992

[51] Int. Cl.[5] ..... A01H 5/00
[52] U.S. Cl. ..... Plt./43.1
[58] Field of Search ..... Plt. 43.1

*Primary Examiner*—James R. Feyrer
*Attorney, Agent, or Firm*—Godfrey & Kahn

[57] ABSTRACT

A new and distinct variety of clingstone peach tree which is characterized principally as to novelty by a date of harvesting and shipment approximately July 1 through July 5 under the ecological conditions prevailing in the Sacramento Valley of California.

1 Drawing Sheet

BACKGROUND OF THE NEW VARIETY

The present invention relates to a new and distinct variety of peach tree which has been denominated varietally as "Thiara", and more particularly to such a peach tree which produces clingstone fruit which are mature for commercial harvesting and shipment from approximately July 1 to July 5, under the ecological conditions prevailing in the Sacramento Valley of California and which is further distinguished as to novelty by producing a clingstone fruit, the flesh of which is firm, fine-textured, and which has a golden yellow color, and which further has a nearly globose form; the fruit of the subject variety being sweet, mild, and well-balanced in flavor and having a pleasant aroma.

It has long been known that the marketability of peaches can be influenced, to some degree, by numerous factors including its date of harvesting and shipment, as well as its external appearance.

The new and novel variety of peach tree described, herein, is noteworthy for producing an attractively colored, early season clingstone peach which is ripe for commercial harvesting and shipment from approximately July 1 to July 5 under the environmental conditions existing in the Sacramento Valley of Calirornia.

ORIGIN AND ASEXUAL REPRODUCTION OF THE NEW VARIETY

The present variety of peach tree was discovered as an open pollinated seedling of unknown parentage growing within the cultivated area of the applicant's ranch which is located at the northwest corner of Carlson Road, and O'Banion Road, in Sutter County, near Yuba City, Calif. in 1992. The inventor, at that time, noted the novel characteristics of the instant variety of peach tree and marked the chance seedling for further observation.

The first asexual reproduction of the new variety occurred in 1992 when the inventor removed budwood from the chance seedling and budded it into Nemaguard peach rootstock which were then growing in a commercial nursery which is located in Stanislaus County, Calif. The test trees have been continually observed by the inventor and it has subsequently been determined that the budded trees have substantially identical characteristics to those observed in the original chance open pollinated seedling.

SUMMARY OF THE NEW VARIETY

The present peach tree is characterized principally as to novelty by producing good quality, early season, clingstone peaches. Most notably, the present variety of peach tree bears a clingstone peach which is ripe for commercial harvesting and shipment from approximately July 1 through July 5 under the environmental conditions existing in the Sacramento Valley of California. The present variety is most closely similar to the unpatented "Loadel" peach tree, but is distinguishable therefrom, and characterized principally as to novelty by being ripe for commercial harvesting and shipment at least eight days earlier than the "Loadel" variety at the same geographical location, and which further produces fruit which are larger and more uniform in size, and which additionally has a more oblate shape, as compared to the shape of the fruit produced by the unpatented Loadel variety which appears more nearly ovate.

BRIEF DESCRIPTION OF THE DRAWINGS

The accompanying drawing is a color photograph of a characteristic twig bearing typical leaves; several mature fruit showing their external coloration sufficiently mature for harvesting and shipment; one fruit of the subject variety dissected in the axial plane to illustrate the flesh characteristics thereof; and one stone; all of the subject variety.

DETAILED DESCRIPTION

Referring more specifically to the pomological details of this new and distinct variety of peach tree, the following has been observed under the ecological conditions prevailing at the orchard of the inventor which is located near Yuba City, Calif. All major color code designations are by reference to the dictionary of color by Maerz and Paul, first edition, 1930. Common color names are also employed occasionally.

TREE

Generally:

*Size.*—Average. The tree is described in the orchard of origin which is located in Stanislaus County, Calif. As noted earlier, budwood was grafted into Nemaguard peach rootstock which is growing in the same orchard and which has an age of less than five years. This rootstock has an average height of about 10 feet and a spread of approximately the same amount.

*Form.*—Upright to upright-spreading, with the eventual form and density determined by pruning.

*Productivity.*—Productive and hardy under typical Sacramento Valley climatic conditions. Vigor: Virorous. Terminal growth in the present orchard for 1992 was approximately 24 inches.

*Regularity of bearing.*—Regular.

Trunk:

*Size.*—Average in thickness.

*Surface texture.*—Moderately rough with numerous broad, flat, bark lenticels, and moderate amounts of scarfskin.

*Color.*—Medium brown-gray, (7-C-10 Kermanshah Brown). Lenticels: Size — Average, approximately 150 of an inch [3.175 millimeters]. Shape — oval. Density — dense.

Branches:

*Size.*—Average in thickness.

*Surface texture.*—Nearly smooth.

*Color of mature branches and shoots.*—Variable from a medium brown-green, (15-L-12 Partridge Brown); to a lighter green-brown, (15-L-7 Willow).

*Color of current season shoots.*—Pale green, (18-G-6).

*Color of current season shoot tips.*—Light, bright green, (18-L-6 Lovebird Green).

LEAVES

Size.

*Generally.*—Medium to large.

*Average length.*—Approximately 17 through 19.6 millimeters, including the petiole.

*Average width.*—Approximately 4.4 to 5.0 centimeters. Internode Length; Variable, 8.89 centimeters to approximately 16.51 centimeters [3.5 inches to approximately 6.5 inches].

Thickness: Average.

Leaf texture: Glabrous.

Leaf form:

*Generally.*—Lanceolate.

Leaf-tip:

*Form.*—Acuminate; a large percentage of the leaf tips twist sideways.

Leaf color:

*Upwardly disposed surfaces.*—Moderately dark green, (24-L-6).

*Downwardly disposed surface.*—Gray-green, (22-K-6, Cress Green).

Leaf margins:

*Form.*—Crenate. The crenations are regular, low, and wide. Near mid-leaf, the crenations may appear doubly so. The leaf margins are moderately undulate and the leaf, as a general matter, generally rolls inwardly from the margins. Additionally, the entire leave recurves downwardly.

Leaf petiole:

*Size.*—Average.

*Length.*—Approximately 10 to 13 millimeters.

*Thickness.*—Approximately 2 millimeters.

*Color.*—Pale green, (19-J-4), and further having a darker petiole groove, (20-K-6 Piquant Green).

Leaf glands:

*Size.*—Medium to below average.

*Shape.*—Globose, although other forms may be observed.

*Numbers.*—One to four stalked glands are observed on the leaf petiole and are located just below the basal leaf margin. As many as two aditional glands may be present on the base of the leaf margin.

*Position.*—Alternate.

*Color.*—Shiny Green when new (19-L-5, Cosse Green); this color, however, darkens with senescence.

Leaf stipules:

*Size.*—Average, approximately 10–12 mm in length; the variety is considered early deciduous.

*Form.*—Lanceolate, and having serrated margins.

*Color.*—Bright Green when appearing as new growth, (18-K-5); but becoming darker with senescence.

FLOWERS

Generally: The flowers appear generally undistinguishable from the unpatented Loadel variety when trees, grown under the same ecological conditions, are compared. The variety is considered self-fruitful.

Bloom timing: In relative comparison to other clingstone peach varieties, the bloom timing is considered normal. Date of full bloom in 1993 was March 12.

Individual flower size: As a general matter, the flowers of the new variety are considered average in size. The diameter of a fully expanded flower ranges in size from approximately 17 to 20 millimeters.

Flower form: The variety is considered non-showy.

Quantity of bloom: The new variety of peach tree described herein has a heavy bloom.

Flowers per node: Variable, having from two to three flowers per node. However, most commonly, two flowers are found.

Petals:

*Size.*—As a general matter, the petal size is considered average.

*Petal length.*—Approximately 10–12 millimeters.

*Petal width.*—Approximately 7–9 millimeters.

*Numbers of petals.*—5 Petals are present per inflorescence.

*Petal form.*—Variable, appearing ovate and at times obovate.

*Petal color.*—This color is considered light pink overall [1-E-1] with a darker rose — pink color appearing basally and along the petal margin [1-I-2]. The color becomes slightly darker and much more dull with advancing senescence.

*Petal claw.*—Form — Truncate.

*Petal apex.*—Shape — Rounded.

*Petal margin.*—Shape — undulate with the petal often appearing cupped inwards.

Pedicel:

*Size.*—Short.

*Average length.*—Approximately 2 millimeters.

*Average thickness.*—Approximately 2 millimeters.

*Color.*—Green [19-L-4].

*Surface texture.*—Glabrous.

Nectaries:

*Color.*—Orange [10-L-2]. The floral nectary color becomes slightly darker with advancing senescence.

Flower anthers:

*Size.*—Medium.

*Color.*—Red, ventrally [1-L-10], and having a light chamois color dorsally [10-E4].

Pollen: As a general matter, pollen is present in abundant amounts. The pollen color is a yellow-gold [10-L-3].

Flower stamens:

*Length.*—Variable, having a range of approximately 8 to 14 millimeters.

Filament color: Light pink when young [1-D-7] and darkening with advancing senescence to a pink-violet color [4-H-4].

Stamen length: Variable, with the longest stamens being slightly longer than the pistil.

Pistil:

*Length.*—Approximately 13 to 14 millimeters including the ovary.

*Coloration.*—Light yellow-green [19-H-1].

*Surface texture.*—Pubescent.

FRUIT

Maturity when described: Ripe for commercial harvesting and shipment approximately July 1 through July 5 under the ecological conditions prevailing at Yuba City, Calif.

Size:

*Generally.*—Large.

*Uniformity.*—Uniform.

*Average axial diameter.*—Approximately 63 to 68 millimeters.

*Average suture diameter.*—Approximately 70 to 73 millimeters.

*Average cheek diameter.*—Approximately 67 to 72 millimeters.

Form:

*Generally.*—Asymmetrical, with one-half of the fruit appearing slightly larger than the other half. The fruit most frequently appears moderately oblate, and occasionally globose in its lateral aspect. Occasionally, the fruit appears globose to slightly oval in its apical aspect.

Suture: The suture appears as a distinct but continuous groove which extends from the base to the apex. The suture otherwise appears slightly folded within the cavity basin.

*Color.*—The suture takes on the coloration of the underlying blush or ground coloration.

Ventral surface:

*Texture.*—Relatively smooth and having a moderate amount of lipping.

Stem cavity:

*Size.*—Average.

*Width.*—Approximately 33 to 35 millimeters.

*Length.*—Approximately 27 to 28 millimeters.

*Form.*—Oval.

*Depth.*—Approximately 16 to 18 millimeters.

Base:

*Shape.*—Somewhat variable, appearing rounded and occasionally slightly truncate.

*Angle.*—Variable, appearing from a right angle to slightly oblique to the fruit axis.

Fruit apex:

*Generally.*—Depressed, and usually recessed within the suture groove. Further, there are depressions on both sides of the apex along the suture line.

Pistil point:

*Position.*—Frequently oblique.

Fruit stem:

*Average length.*—Medium, approximately 5 to 7 millimeters.

*Thickness.*—Approximately 3 to 3.5 millimeters.

*Coloration.*—Variable, from a light green (20-L-3 Certosa Green) to a light green — brown (14-L-2 Old Moss).

Skin thickness: Moderately thick.

skin pubescence: The fruit is uniformly colored with a fine lightly colored pubescence. The hairs are of medium length.

Skin flavor: Considered mild with very little acidity.

Tenacious to flesh: Yes.

Tendency to crack: Not observed.

Skin color:

*Generally.*—Variable, having from approximately 5% to approximately 40% of the surface areas are colored. The color pattern is variable at times, that is, it is lightly striped with spots of red. At other times, a blush color appears. The red appearing in the skin color ranges from approximately a medium, red-orange (2-I-11, Flamingo Red) to a darker full red (3-J-11 Flash Red). The ground color of the skin is a uniform, bright, yellow-gold (10-K-6 Chinese Yellow). The yellow ground color covers approximately 60% to about 95% of the fruit surface.

Flesh color:

*Generally.*—Yellow-gold; (10-K-3, Lemon Yellow). The flesh color can appear slightly darker near and in the pit cavity (10-L-5 Primuline Yellow).

Fibers:

*Generally.*—A moderate number of tender white fibers are present throughout the fruit. No staining of the pit cavity was observed for the fruit examined in 1992.

Flesh texture:

*Generally.*—The subject variety is considered to be firm, and fine. The flesh is also considered to be of a non-melting variety.

Ripening:

*Generally.*—The variety appears to ripen uniformly.

Flavor:

*Generally.*—Pleasant, sweet, mild, and well-balanced.

Aroma: Moderate and pleasant.

Eating quality: Considered very good.

Use: The present variety of peach tree produces fruit which are suitable for canning purposes.

Storage and keeping qualities: The firm nature of the flesh of the present variety of peach tree at commercial maturity tends to indicate that the variety will have acceptable storage characteristics. In view of the anticipated use of this fruit for canning, no substantial storage or shipment problems is anticipated.

STONE

Attachment: Clingstone. The stone of the subject variety is tightly attached, both laterally and along both sutures.

Fibers:

*Generally.*—Numerous short, light-colored fibers are present.

Size:

*Generally.*—Medium to large.

*Average length.*—Approximately 30 to 34 millimeters.

*Average width.*—Approximately 26 to 27 millimeters.

*Average thickness.*—Approximately 19 to 21 millimeters.

Stone form:

*Generally.*—Variable. Most frequently oval, although at times the stone appears to be slightly obovate.

Base:

*Generally.*—Slightly truncate. As a general matter, the stone base is most frequently at right angles to the stone axis.

Hilum:

*Generally.*—Average in size; oval in shape; and usually appears heavily eroded.

Stone apex:

*Generally.*—Rounded in form and having a varibly shaped tip. The tip, as a general matter, can range from rounded to acute.

Stone sides:

*Shape.*—Unequal.

Stone surface:

*Texture.*—Grooved, and pitted laterally. The grooves are most apparent over the apical shoulders. Numerous irregular shaped pits are present in the lateral aspect.

Ventral edge:

*Generally.*—The ventral edge is broad and is approximately 5 to 6 millimeters in width, when measured at mid-suture. Several low, coalesced wings are present. The wings converge apically.

Dorsal edge:

*Generally.*—The dorsal edge appears narrow and raised. A medium sized groove is normally present and extends from the base to the apex. This groove is relatively uniform along its entire length. Normally, the groove is subtended by two high, raised and prominent ridges. These ridges are cut in several places by deep cross-grooves. The dorsal ridges are somewhat lower in height, and are positioned approximately 7 to 10 millimeters below the apex.

Stone color:

*Dry.*—A uniform, light beige (11-F-6).

Tendency to split: Not observed in 1992.

Use: A high quality clingstone peach with an early date of maturity suitable for use as a canning peach and for other processing.

Resistance to disease: Average as compared with other varieties.

As will be appreciated, the new variety of peach tree possesses the described characteristics when grown under the ecological conditions prevailing in the Sacramento Valley of California. It is to be understood, however, that variations of the usual magnitude and characteristics incident to changes and growing conditions, fertilization, pruning and pest control are to be expected.

Having thus described and illustrated my new variety of peach tree, what is claimed as new and desired to be secured by plant Letters Patent is:

1. A new and distinct variety of peach tree substantially as illustrated and described and which is somewhat similar to the Loadel variety of peach tree (unpatented) with which it is somewhat closely similar in its physical appearance, but which is distinguished therefrom, and characterized principally as to novelty by bearing fruit which are ripe for commercial harvesting and shipment approximately July 1 through July 5 in the Sacramento Valley of California, and which further produces a clingstone fruit which has a good flavor, an attractive skin coloration, a larger size, and a date of maturity which is approximately 8 days earlier than the Loadel peach tree at the same geographical location.

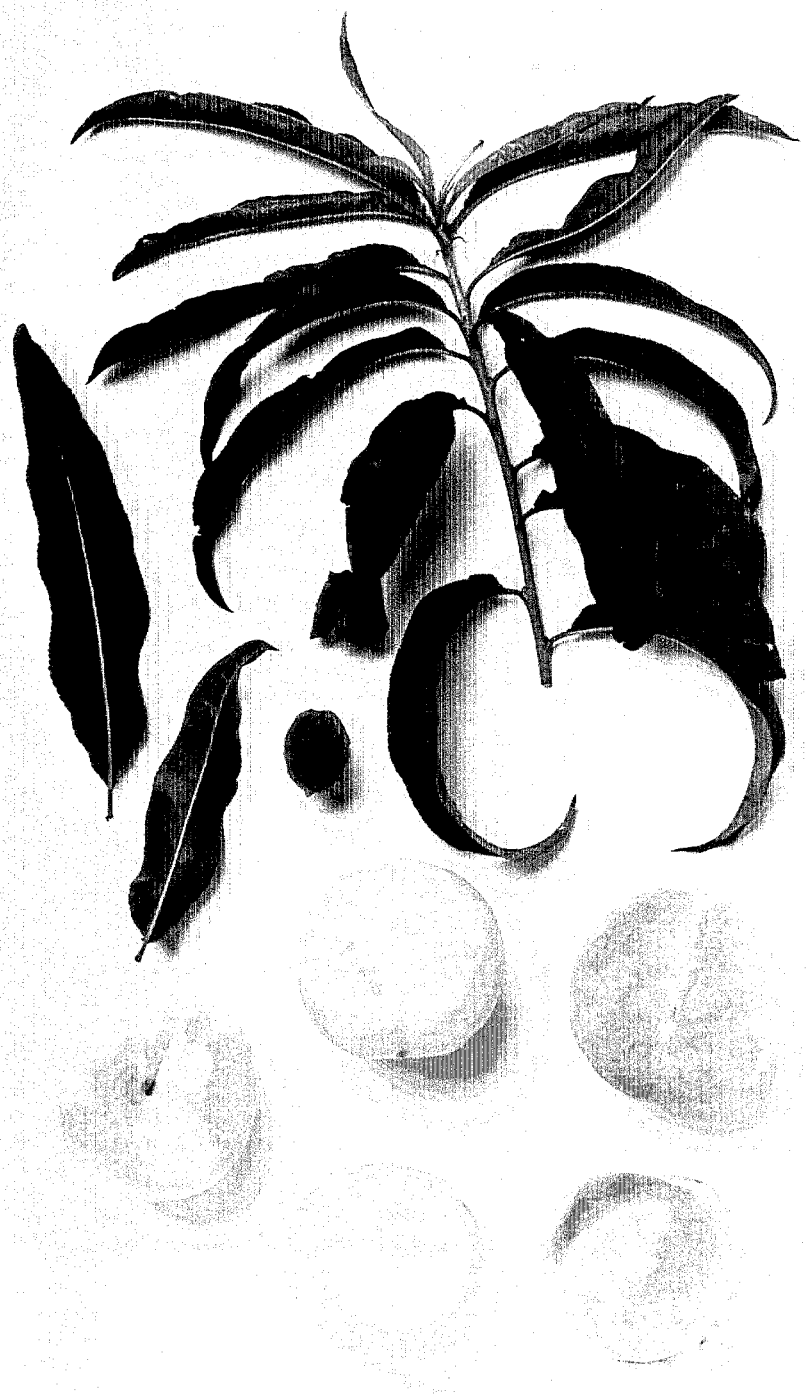

* * * * *